(12) United States Patent
Kato et al.

(10) Patent No.: US 9,194,788 B2
(45) Date of Patent: Nov. 24, 2015

(54) CORROSION DETECTION SENSOR DEVICE

(75) Inventors: Juri Kato, Nagano (JP); Takao Miyazawa, Shimosuwa-machi (JP)

(73) Assignee: Seiko Epson Corporation, Tokyo (JP)

( * ) Notice: Subject to any disclaimer, the term of this patent is extended or adjusted under 35 U.S.C. 154(b) by 259 days.

(21) Appl. No.: 13/458,247

(22) Filed: Apr. 27, 2012

(65) Prior Publication Data

US 2012/0286804 A1  Nov. 15, 2012

(30) Foreign Application Priority Data

May 13, 2011  (JP) .................................. 2011-107934

(51) Int. Cl.
| | |
|---|---|
| *G01N 27/02* | (2006.01) |
| *G01N 27/26* | (2006.01) |
| *G01N 27/416* | (2006.01) |
| *G01N 33/20* | (2006.01) |
| *G01N 33/38* | (2006.01) |
| *G01N 17/02* | (2006.01) |
| *G01N 27/12* | (2006.01) |
| *G01N 27/04* | (2006.01) |

(52) U.S. Cl.
CPC ............... *G01N 17/02* (2013.01); *G01N 27/048* (2013.01); *G01N 27/125* (2013.01); *G01N 27/4167* (2013.01); *G01N 33/383* (2013.01); *G01N 33/20* (2013.01)

(58) Field of Classification Search
CPC ..... G01N 17/02; G01N 17/04; G01N 27/002; G01N 27/223; G01N 27/414; G01N 33/383; G01N 27/048; G01N 17/006; G01N 2291/02845; G01N 2291/0232; G01N 27/125; G01N 27/4167; G01N 33/20

USPC ......... 324/700, 693, 691, 647, 649, 690, 713, 324/717, 718; 204/404
See application file for complete search history.

(56) References Cited

U.S. PATENT DOCUMENTS 3,817,795 A * 6/1974 Pourbaix ........................ 148/241
5,792,337 A * 8/1998 Padovani et al. ............ 205/775.5
(Continued)

FOREIGN PATENT DOCUMENTS

| JP | 06-222033 A | 8/1994 | |
| JP | 09171012 A * | 6/1997 | ............. G01N 33/38 |

(Continued)

OTHER PUBLICATIONS

B. Yang et al.; Compliant and low-cost humidity nanosensors using nanoporous polymer membranes; Sensors and Actuators B: Chemical; vol. 114, Issue 1, Mar. 30, 2006, pp. 254-262.*

(Continued)

*Primary Examiner* — Huy Q Phan
*Assistant Examiner* — James Split
(74) *Attorney, Agent, or Firm* — Global IP Counselors, LLP

(57) ABSTRACT

A sensor device includes a first electrode, a second electrode and a functional element. The first electrode includes a porous body having a connecting hole where adjacent holes communicate with each other with the porous body being in at least the vicinity of a surface of the first electrode. The second electrode is spaced apart from the first electrode. The functional element is configured to measure a difference in electric potential between the first electrode and the second electrode. The sensor device is configured to measure a state of a site to be measured based on the difference in electric potential as measured by the functional element.

8 Claims, 12 Drawing Sheets

(56) References Cited

U.S. PATENT DOCUMENTS

| | | | |
|---|---|---|---|
| 6,796,187 B2 * | 9/2004 | Srinivasan et al. | 73/784 |
| 6,828,808 B2 * | 12/2004 | Srinivasan et al. | 324/693 |
| 7,034,660 B2 * | 4/2006 | Watters et al. | 340/10.41 |
| 7,063,781 B2 * | 6/2006 | Murray et al. | 205/789 |
| 7,148,706 B2 * | 12/2006 | Srinivasan et al. | 324/700 |
| 7,378,852 B2 * | 5/2008 | Brinz et al. | 324/438 |
| 8,016,991 B2 * | 9/2011 | Scheying et al. | 204/433 |
| 2006/0006137 A1 * | 1/2006 | Niblock | 216/41 |
| 2006/0170535 A1 * | 8/2006 | Watters et al. | 340/10.41 |
| 2008/0252207 A1 * | 10/2008 | Yamazaki et al. | 313/504 |
| 2010/0263462 A1 * | 10/2010 | Nakamura | 73/866.5 |
| 2012/0000285 A1 * | 1/2012 | Waga et al. | 73/335.04 |
| 2012/0206156 A1 * | 8/2012 | Karakaya | 324/705 |

FOREIGN PATENT DOCUMENTS

| | | |
|---|---|---|
| JP | 09-329568 A | 12/1997 |
| JP | 2008128734 A * | 6/2008 |
| JP | 2011-022032 A | 2/2011 |
| JP | 2011-022982 A | 2/2011 |
| WO | WO 2010113712 A1 * | 10/2010 |

OTHER PUBLICATIONS

Horiguchi et al.; "Quantitative Estimation for Amount of Steel Bar Corrosion with Salt Attack—Amount of Steel Bar Corrosion Estimated by Crack Width and Concrete Surface Rising-" Report of Taisei Technology Center No. 37; 2004.

* cited by examiner

CORROSION DETECTION SENSOR DEVICE

CROSS-REFERENCE TO RELATED APPLICATIONS

This application claims priority to Japanese Patent Application No. 2011-107934 filed on May 13, 2011. The entire disclosure of Japanese Patent Application No. 2011-107934 is hereby incorporated herein by reference.

BACKGROUND

1. Technical Field

The present invention relates to a sensor device.

2. Related Art

There are known sensor devices which, for example, measure the state of corrosion of a reinforcing bar in concrete (e.g., see Japanese Laid-Open Patent Publication 6-222033).

Typically, the concrete in a concrete structure immediately after construction exhibits a strong alkalinity. For this reason, the reinforcing bars in a concrete structure immediately after construction have a passivation film formed on the surface thereof and are therefore safe. However, in concrete structure that is affected after construction by acid rain, exhaust gas, and the like, the concrete will be gradually acidified, and the reinforcing bars will therefore corrode.

For example, in the device recited in the above mentioned publication, a probe provided with a reference electrode and a counter electrode is embedded in concrete and measures the polarization resistance and changes in electric potential caused by the corrosion of the reinforcing bars, whereby the corrosion of the reinforcing bars is predicted.

In such a device, the reference electrode and the counter electrode embedded in the concrete are used to measure the self-potential of the reinforcing bars, which are used as a working electrode, but a corrosion response does not progress when the surfaces of the reinforcing bars do not have sufficient moisture. For this reason, in some cases, when the surfaces of the reinforcing bars do not have sufficient moisture, even though a reinforcing bar may have a corroded region, no difference (gradient) in electric potential between the corroded region and the non-corroded region occurs. In view of such a fact, in the device recited in the above mentioned publication, a fluctuation in moisture inside the concrete has a major impact and there is a variance to the self-potential (gradient) of the reinforcing bars, thus rendering it difficult to accurately predict the corrosion of the reinforcing bars.

SUMMARY

An objective of the present invention is to provide a sensor device with which it is possible, after reinforcing bars have been constructed, to measure changes in the state of an object to be measured during the period up until corrosion begins, and to use the resulting information in planning the preservation of the concrete structure.

Such an objective is achieved by the present invention described below.

A sensor device according to one aspect of the present invention includes a first electrode, a second electrode and a functional element. The first electrode includes a porous body having a connecting hole where adjacent holes communicate with each other with the porous body being in at least the vicinity of a surface of the first electrode. The second electrode is spaced apart from the first electrode. The functional element is configured to measure a difference in electric potential between the first electrode and the second electrode. The sensor device is configured to measure a state of a site to be measured based on the difference in electric potential as measured by the functional element.

According to the sensor device having such a configuration, the surface area of the first electrode can be increased because the connecting holes (fine pores) open onto the surface of the first electrode. For this reason, the amount of moisture adhering to the first electrode can be increased.

Further, the capillary condensation effect originating from the connecting holes (fine holes) opening on the surface of the first electrode makes it possible to cause moisture to condense on the first electrode at a lower relative humidity. For this reason, a stable presence of liquid water can be maintained on the first electrode.

In view of such a fact, a fluctuation in the amount of moisture on the first electrode can be prevented even though the relative humidity of the site to be measured may change in association with changes in the humidity or temperature of the external environment. Consequently, changes in the humidity or temperature of the external environment can be prevented from causing the self-potential of the first electrode to fluctuate, and the state of the site to be measured can be measured with a high degree of precision.

In the sensor device according to the above described aspect of the present invention, the second electrode preferably includes a porous body having a connecting hole where adjacent holes communicate with each other with the porous body being in at least the vicinity of a surface of the second electrode.

This makes it possible to prevent a fluctuation in the amount of moisture on the second electrode even though the relative humidity of the site to be measured may change in association with changes in the humidity or temperature of the external environment. Consequently, changes in the humidity or temperature of the external environment can be prevented from causing the self-potential of the second electrode to fluctuate, and the state of the site to be measured can be measured with a high degree of precision.

In the sensor device according to the above described aspect of the present invention, the first electrode preferably includes a first metallic material in which either a first passivation film is formed on a surface thereof or a first passivation film present on a surface thereof is lost, in association with changes in an environment of the site to be measured.

Thereby, the difference in electric potential between the first electrode and the second electrode has sharp changes depending on the presence or absence of the first passivation film as associated with changes in the pH of the site to be measured. For this reason, it is possible to accurately measure whether or not the pH of the site to be measured is at or below a set value.

The difference in electric potential between the first electrode and the second electrode also has sharp changes depending on the loss of the first passivation film, which is associated with a change in the chloride ion concentration of the site to be measured. For this reason, it is possible to accurately measure whether or not the chloride ion concentration of the site to be measured is at or below a set value.

In the sensor device according to the above described aspect of the present invention, the second electrode preferably includes a second metallic material in which either a second passivation film is formed on a surface thereof or a second passivation film present on a surface thereof is lost, in association with changes in the environment of the site to be measured.

Thereby, the difference in electric potential between the first electrode and the second electrode has sharp changes depending on the presence or absence of the second passivation film as associated with changes in the pH of the site to be measured. For this reason, it is possible to accurately measure whether or not the pH of the site to be measured is at or below a set value.

The difference in electric potential between the first electrode and the second electrode also has sharp changes depending on the loss of the second passivation film, which is associated with a change in the chloride ion concentration of the site to be measured. For this reason, it is possible to accurately measure whether or not the chloride ion concentration of the site to be measured is at or below a set value.

In the sensor device according to the above described aspect of the present invention, each of the first metallic material and the second metallic material is preferably iron or an iron-based alloy.

Iron or iron-based alloys (iron-based materials) are more readily and more inexpensively procured. In a case where, for example the sensor device is used to measure the state of a concrete structure, then at least one electrode of the first electrode and the second electrode can be constituted of the same material as the reinforcing bars inside the concrete structure, and it is possible to effectively detect the state of corrosion of the reinforcing bars inside the concrete structure.

In the sensor device according to the above described aspect of the present invention, at least one of the first electrode and the second electrode preferably includes a substrate and a conductive film provided on the substrate including a material different from that of the substrate.

This makes it possible for the vicinity of the surface of at least one electrode or more of the first electrode and the second electrode to be constituted of a metal from which it is difficult to produce a porous body. It is also possible to use the thickness of the conductive film to adjust the diameter of the holes of the porous body constituting the at least one electrode or more of the first electrode and the second electrode.

In the sensor device according to the above described aspect of the present invention, preferably, the conductive film preferably includes a metallic material in which either a passivation film is formed on a surface thereof or a passivation film present on a surface thereof is lost, in association with changes in an environment of the site to be measured.

Thereby, the difference in electric potential between the first electrode and the second electrode has sharp changes depending on the presence or absence of the passivation film as associated with changes in the pH of the site to be measured. For this reason, it is possible to accurately measure whether or not the pH of the site to be measured is at or below a set value.

The difference in electric potential between the first electrode and the second electrode also has sharp changes depending on the loss of the passivation film, which is associated with a change in the chloride ion concentration of the site to be measured. For this reason, it is possible to accurately measure whether or not the chloride ion concentration of the site to be measured is at or below a set value.

In the sensor device according to the above described aspect of the present invention, the functional element is preferably further configured to detect whether or not pH or chloride ion concentration at the site to be measured is at or below a set value, based on the difference in electric potential between the first electrode and the second electrode.

This makes it possible to detect the changes in state of an object to be measured which accompany changes in the pH or chloride ion concentration thereof.

The sensor device according to the above described aspect of the present invention preferably further includes an antenna and a communication circuit configured to provide power to the antenna, and the functional element is preferably further configured to drive and control the communication circuit.

This makes it possible to wirelessly transmit measurement results to the outside of the object to be measured.

BRIEF DESCRIPTION OF THE DRAWINGS

Referring now to the attached drawings which form a part of this original disclosure.

DETAILED DESCRIPTION OF EXEMPLARY EMBODIMENTS

The following is a description of preferred embodiments of the sensor device of the present invention, with reference to the accompanying drawings.

First Embodiment

The first embodiment of the present invention shall be described first.

Figure 1:
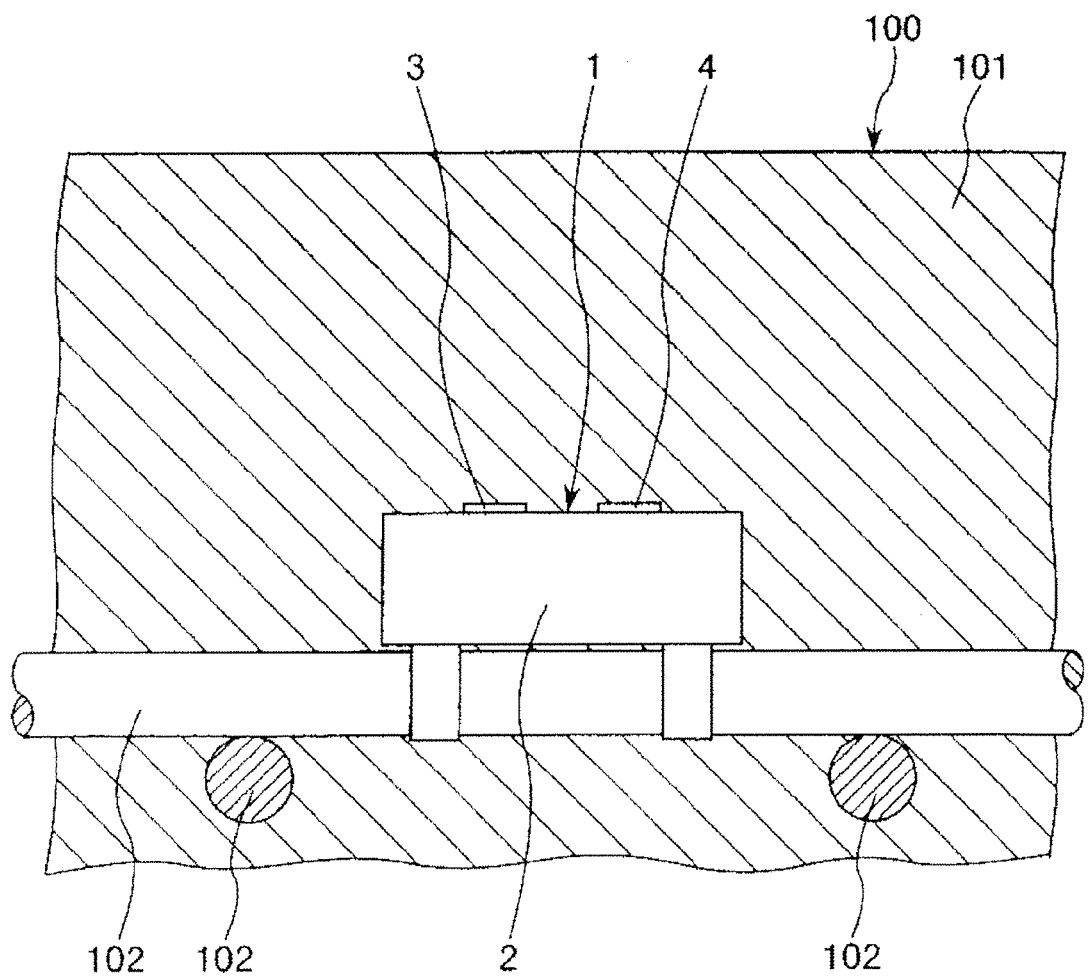
FIG. 1 is a drawing illustrating an example of the state of use of a sensor device according to a first embodiment of the present invention.
Figure 2:
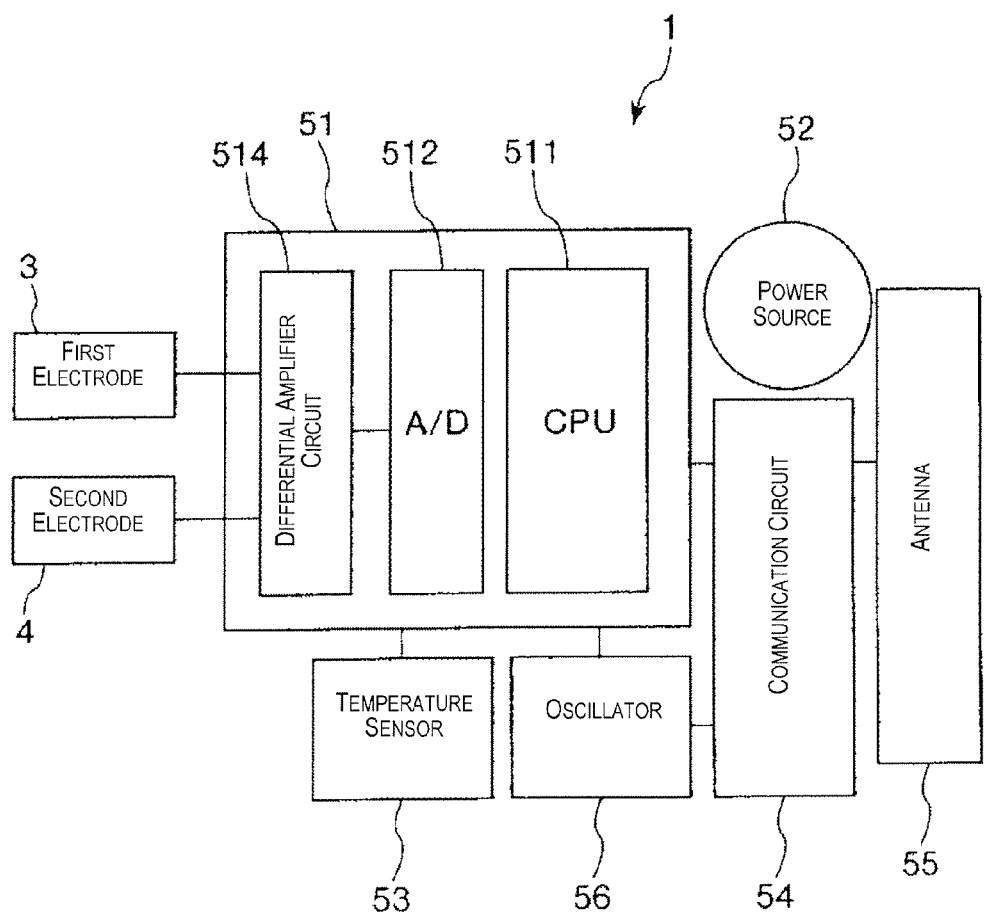
FIG. 2 is a block diagram illustrating a schematic configuration of the sensor device illustrated in FIG. 1.
Figure 3:
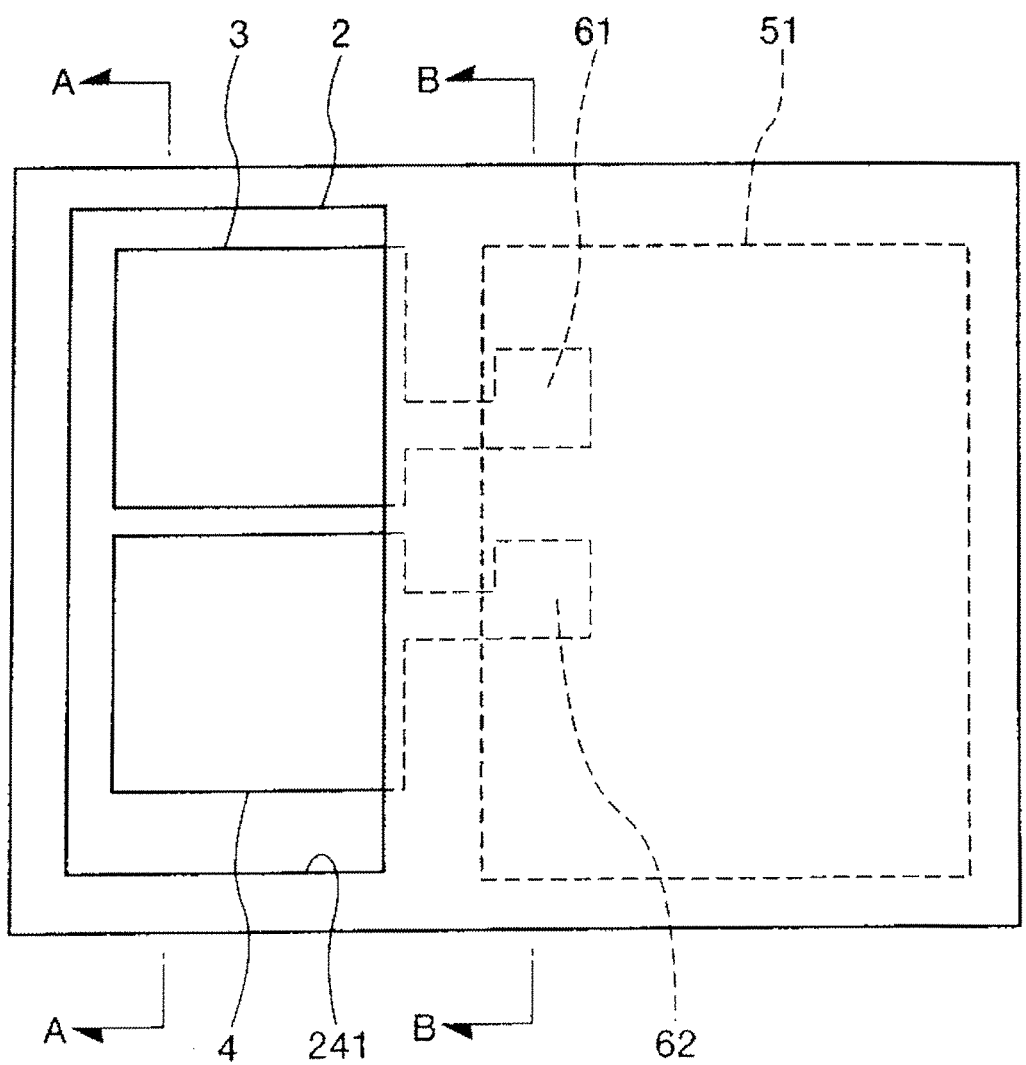
FIG. 3 is a plan view of a first electrode, a second electrode, and a functional element illustrated in FIG. 2.
Figure 4:
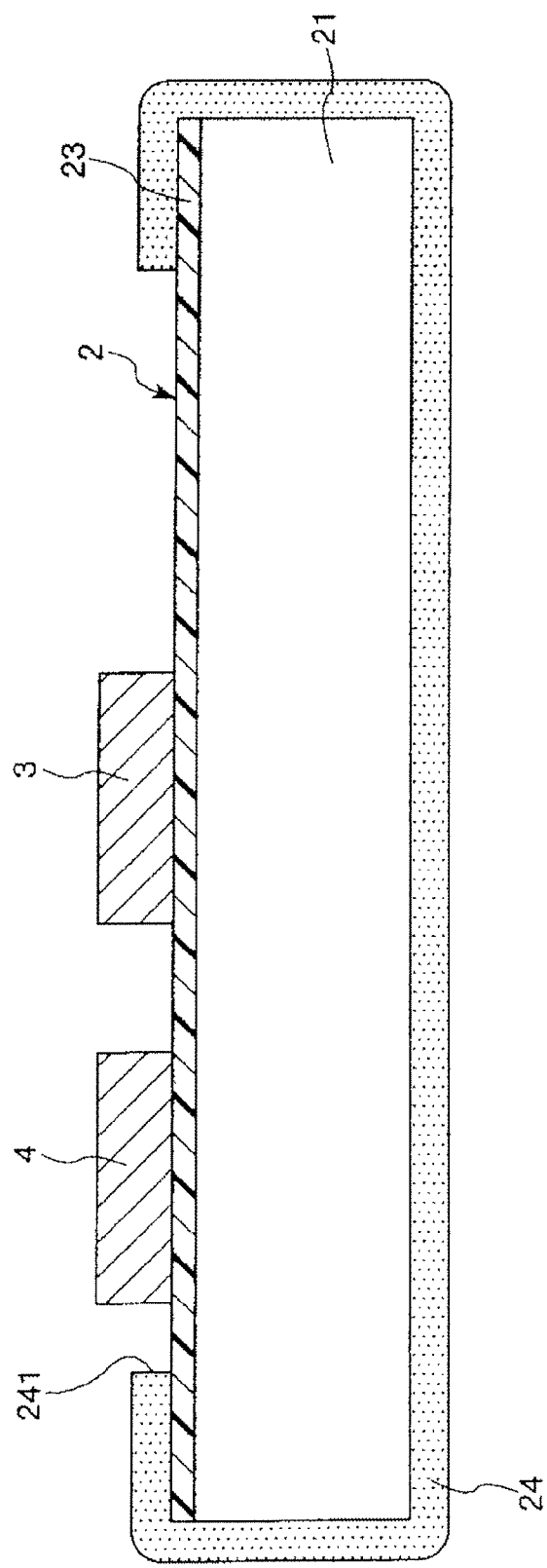
FIG. 4 is a cross-sectional view (a cross-sectional view along line A-A in FIG. 3) for describing the first electrode and the second electrode illustrated in FIG. 2.
Figure 5:
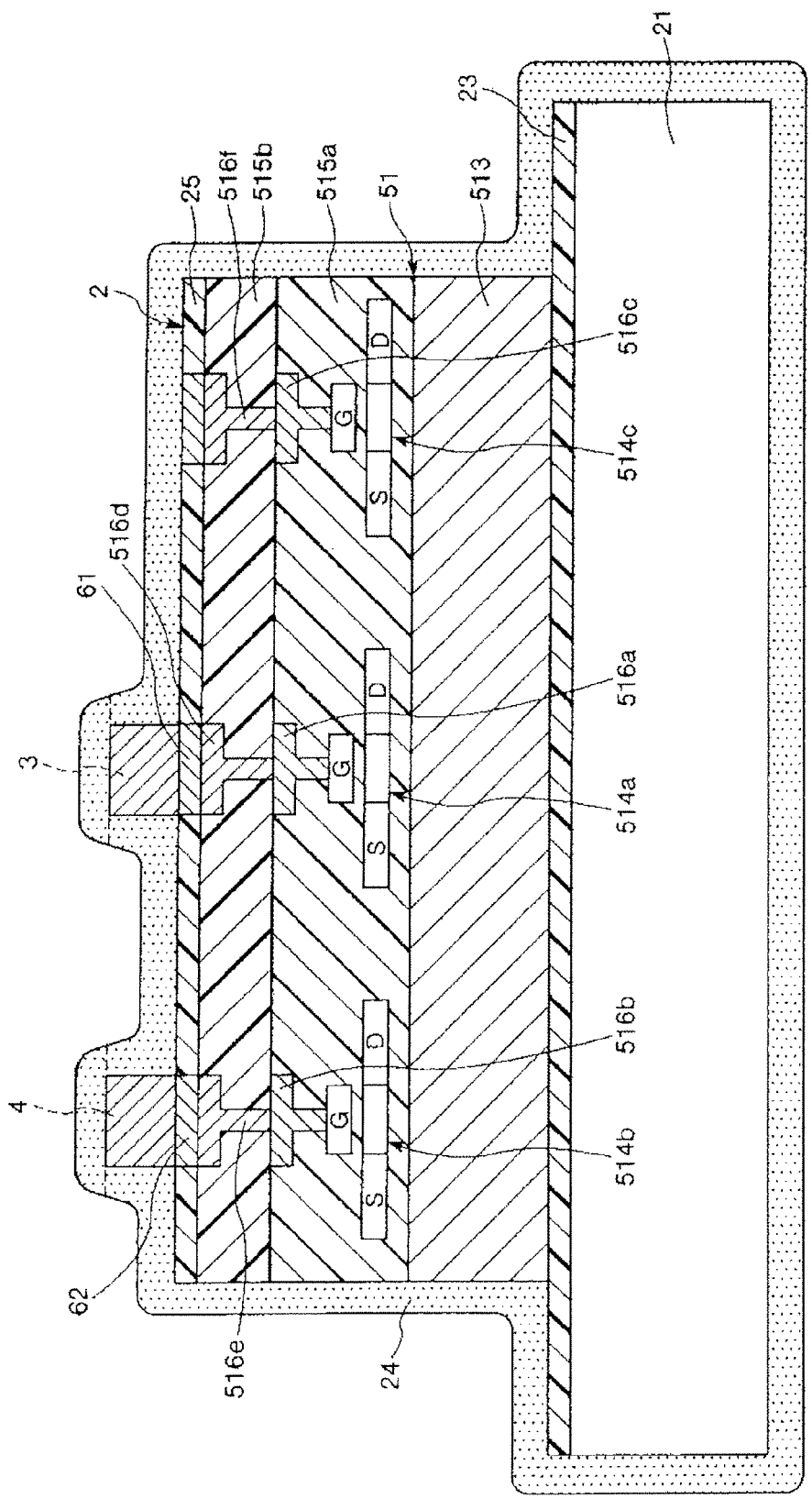
FIG. 5 is a cross-sectional view (a cross-sectional view along line B-B in FIG. 3) for describing the functional element illustrated in FIG. 2.
Figure 6A:
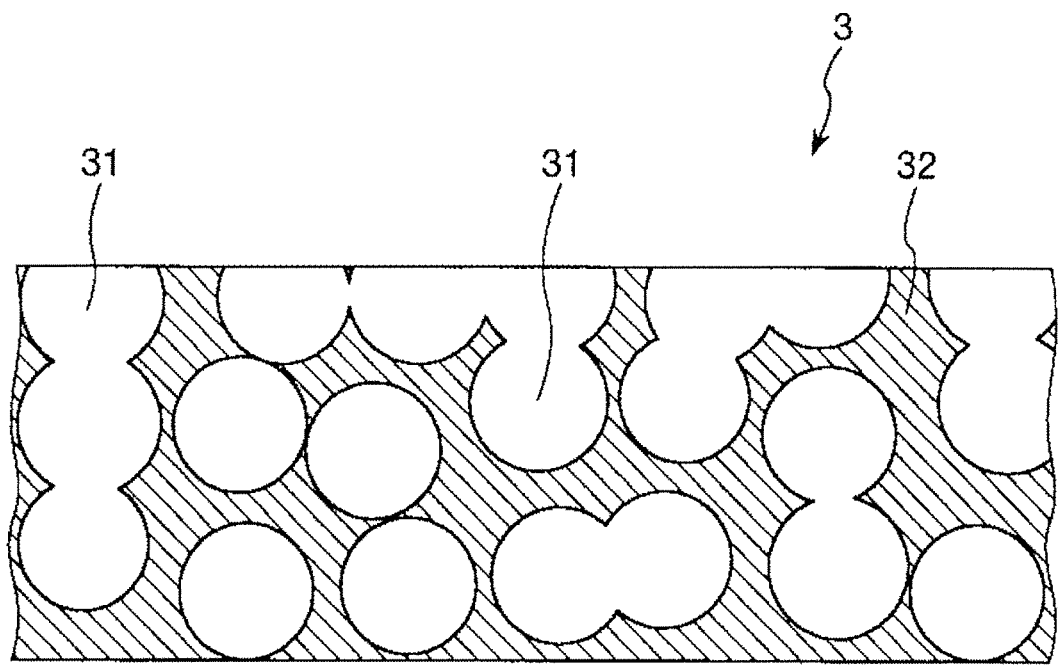
FIG. 6A is an enlarged sectional view illustrating an example of a configuration of the first electrode illustrated in FIG. 2.
Figure 6B:
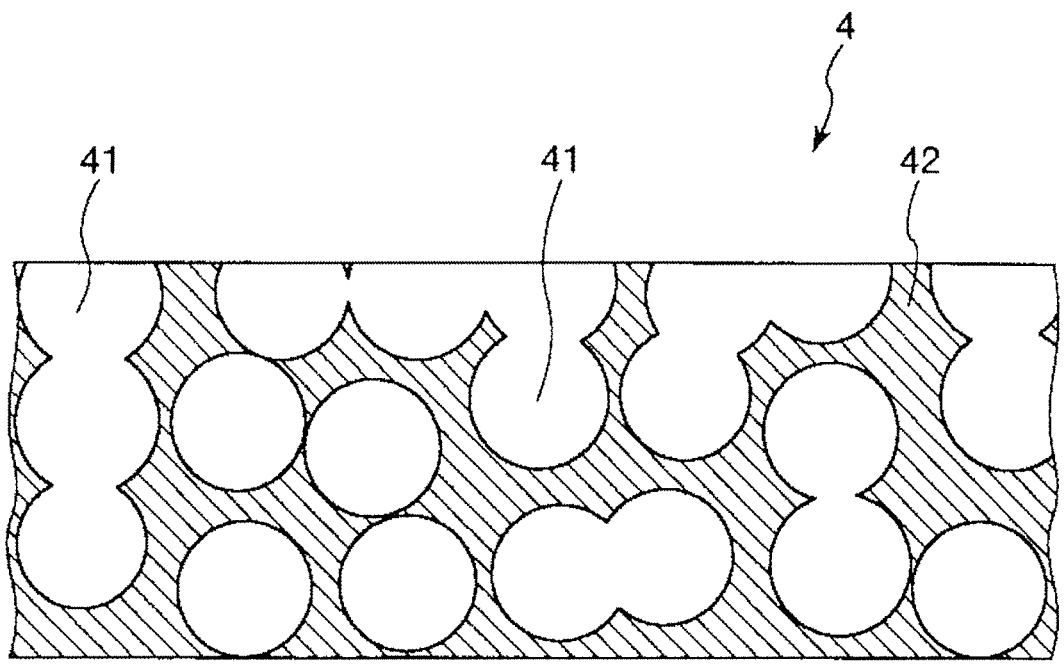
FIG. 6B is an enlarged sectional view illustrating an example of a configuration of the second electrode illustrated in FIG. 2.
Figure 7:
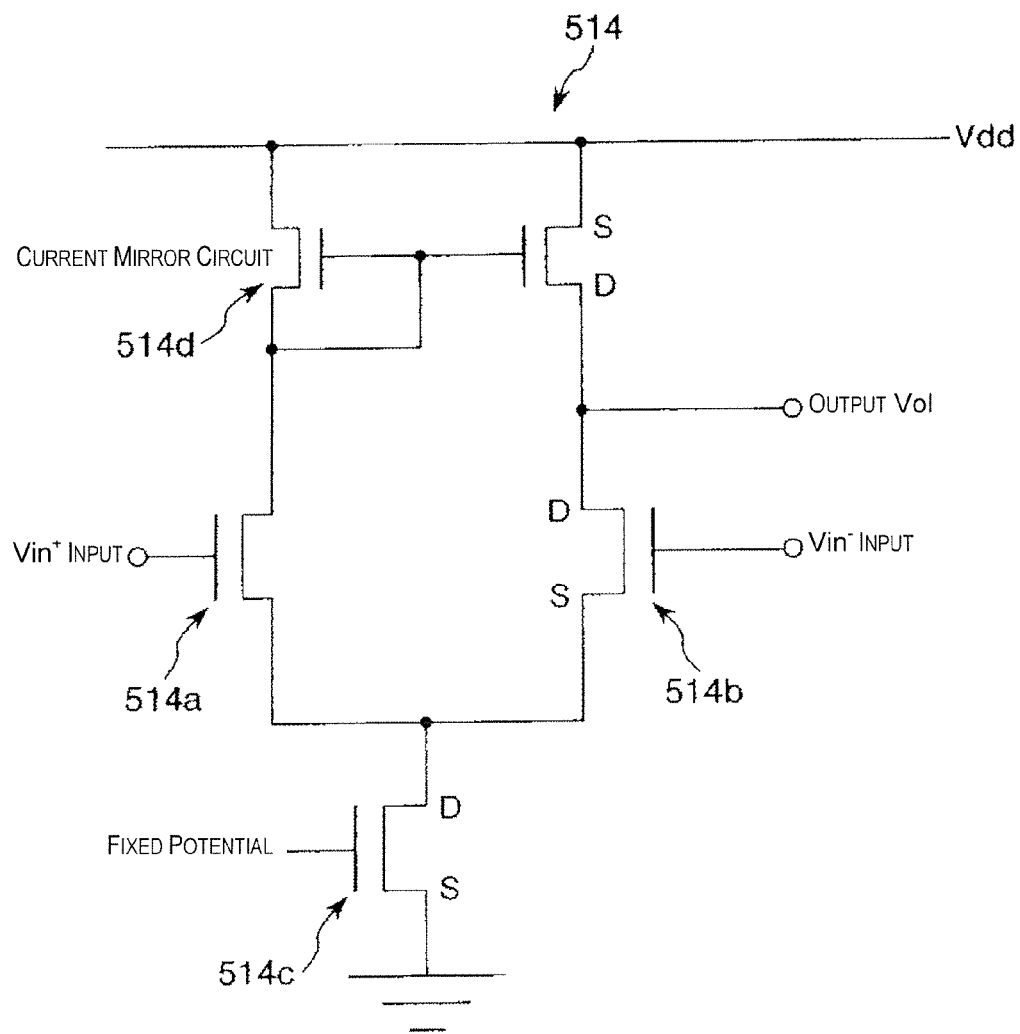
FIG. 7 is a circuit diagram illustrating a differential amplifier circuit provided to the functional element illustrated in FIG. 2.
Figure 8:
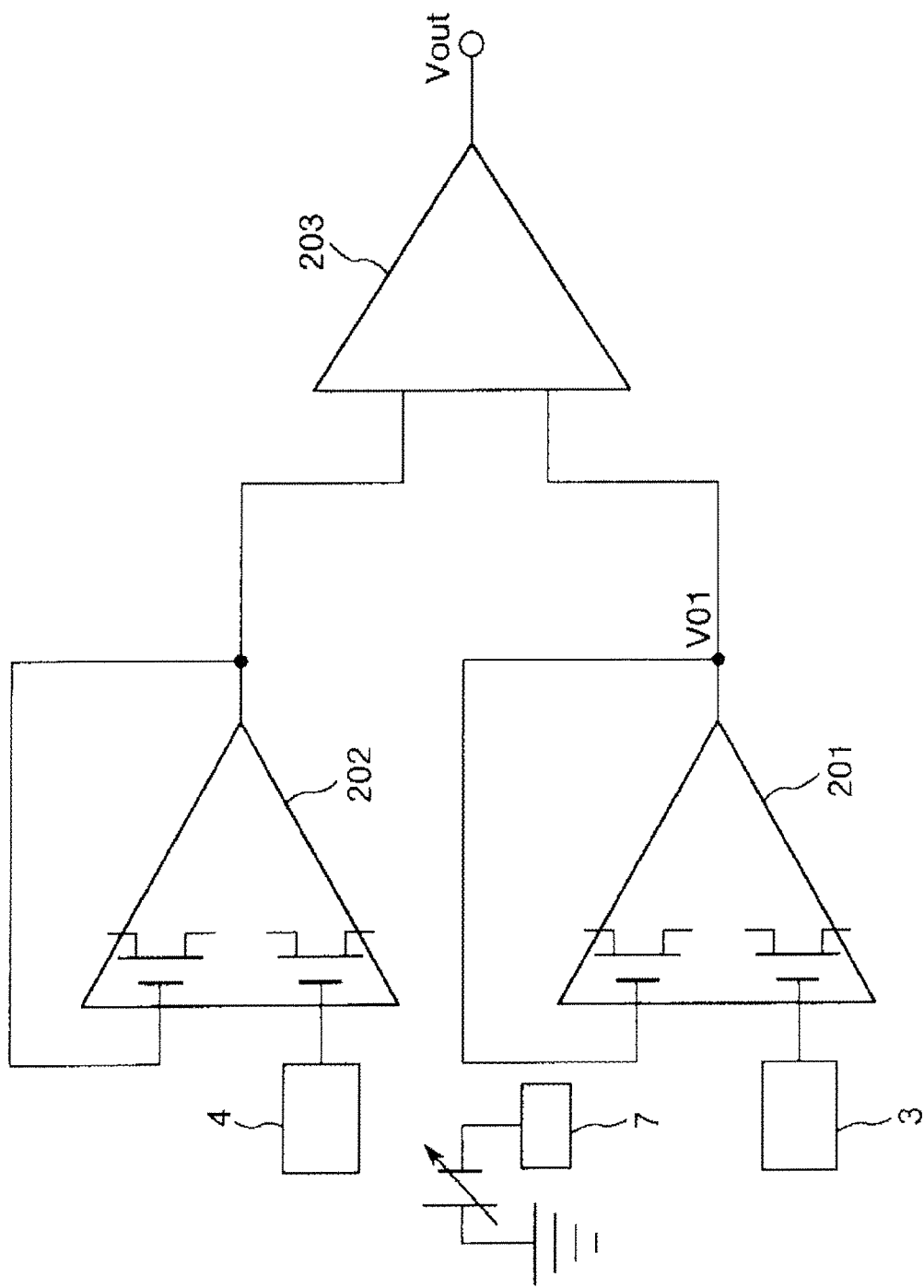
FIG. 8 is a circuit diagram illustrating the differential amplifier circuit provided to the functional element illustrated in FIG. 2.
Figure 9A:
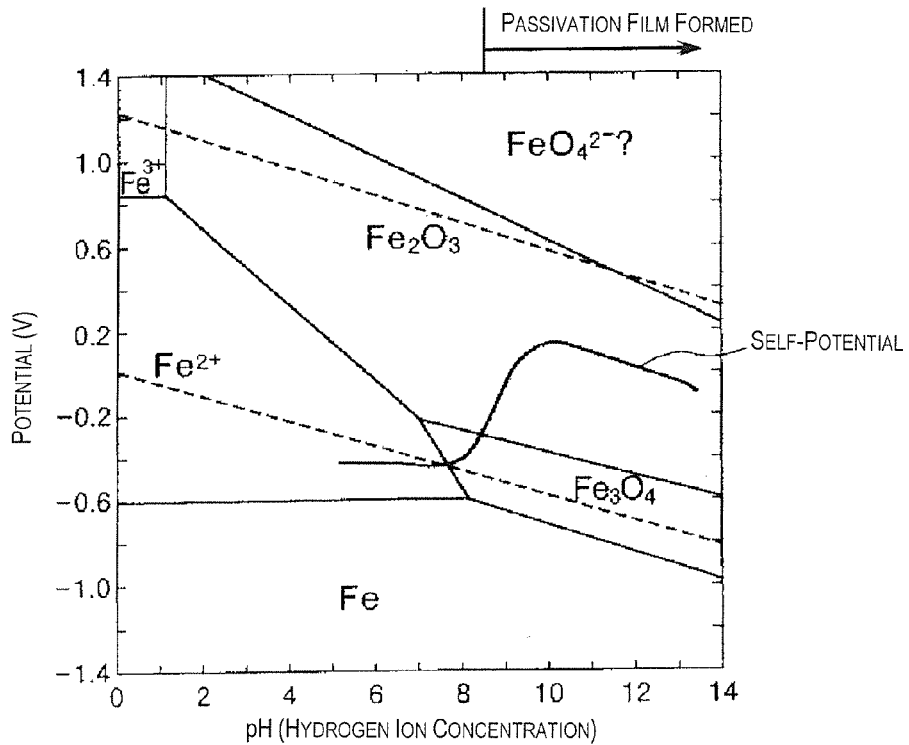
FIG. 9A is a drawing illustrating an example of the manner in which the pH and electric potential of iron is related to the state.
Figure 9B:
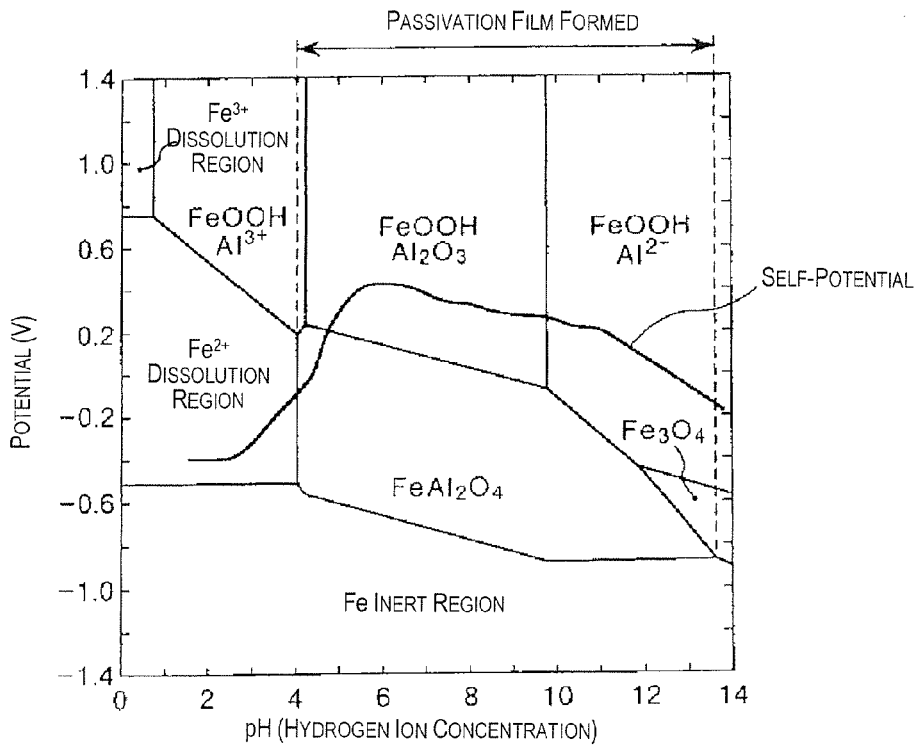
FIG. 9B is a drawing illustrating an example of the manner in which the pH and electric potential of iron-aluminum is related to the state.

FIG. 1 is a drawing illustrating an example of the state of use of a sensor device according to a first embodiment of the present invention. FIG. 2 is a block diagram illustrating a schematic configuration of the sensor device illustrated in FIG. 1. FIG. 3 is a plan view of a first electrode, a second electrode, and a functional element illustrated in FIG. 2. FIG. 4 is a cross-sectional view (a cross-sectional view along line A-A in FIG. 3) of the first electrode and the second electrode illustrated in FIG. 2. FIG. 5 is a cross-sectional view (a cross-sectional view along line B-B in FIG. 3) of the functional element illustrated in FIG. 2. FIG. 6A is an enlarged sectional view illustrating an example of a configuration of the first electrode illustrated in FIG. 2. FIG. 6B is an enlarged sectional view illustrating an example of a configuration of the second electrode illustrated in FIG. 2. FIGS. 7 and 8 are each circuit diagrams illustrating a differential amplifier circuit provided to the functional element illustrated in FIG. 2. FIG. 9A is a drawing illustrating an example of the manner in which the pH and electric potential of iron is related to the state. FIG. 9B is a drawing illustrating an example of the manner in which the pH and electric potential of iron-aluminum is related to the state. FIG. 10 is a drawing for describing an example of the action of the sensor device illustrated in FIG. 1.

The example described below is that of a case where the sensor device of the present invention is used to measure the quality of a concrete structure.

A sensor device 1 shown in FIG. 1 is intended to measure the quality of a concrete structure 100.

The concrete structure 100 has a plurality of reinforcing bars 102 embedded in concrete 101. The sensor device 1 is also embedded within the concrete 101 of the concrete structure 100, in the vicinity of the reinforcing bars 102. The sensor device 1 may be embedded when the concrete structure 100 is being cast, prior to the casting of the concrete 101, so as to be fixed to the reinforcing bars 102, or may be embedded in holes bored into the concrete 101 having hardened after casting.

The sensor device 1 has a main body 2, as well as a first electrode 3 and a second electrode 4 exposed to the surface of the main body 2. In the present embodiment, the first electrode 3 and the second electrode 4 are installed on the outer surface of the concrete structure 100 further out than the reinforcing bars 102 so that both are equidistant from the outer surface of the concrete structure 100. The first electrode 3 and the second electrode 4 are also installed such that the respective electrode surfaces thereof are parallel or substantially parallel to the outer surface of the concrete structure 100. The first electrode 3 and the second electrode 4 are also configured such that the difference in electric potential therebetween changes in association with changes in pH of a site to be measured of the concrete 101. More detailed descriptions of the first electrode 3 and the second electrode 4 shall be provided below.

The sensor device 1, as illustrated in FIG. 2, also has a functional element 51, a power source 52, a temperature sensor 53, a communication circuit 54, an antenna 55, and an oscillator 56, which are electrically connected to the first electrode 3 and to the second electrode 4 and are housed within the main body 2.

The following is a sequential description of each of the parts constituting the sensor device 1.

Main Body

The main body 2 has a function for supporting the first electrode 3, the second electrode 4, the functional element 51, and other elements.

Such a main body 2, as illustrated in FIG. 4 and FIG. 5, has a substrate 21 for supporting the first electrode 3, the second electrode 4, and the functional element 51. The substrate 21 is also intended to support the power source 52, the temperature sensor 53, the communication circuit 54, the antenna 55, and the oscillator 56, but FIGS. 3 to 5 omit a depiction of the power source 52, the temperature sensor 53, the communication circuit 54, the antenna 55, and the oscillator 56, for convenience of description.

The substrate 21 has insulating properties. Examples which can be used as the substrate 21 include, but are not particularly limited to, an alumina substrate, a resin substrate, or the like.

An insulating layer 23 constituted of an insulating resin composition, such as, for example, a solder resist, is provided on the substrate 21. The first electrode 3, the second electrode 4, and the functional element 51 are also mounted onto the substrate 21 via the insulating layer 23.

As illustrated in FIG. 5, the functional element 51 (an integrated circuit chip) is retained on the substrate 21, and conductor parts 61, 62 (an electrode pad) of the functional element 51 are connected to the first electrode 3 and the second electrode 4.

The conductor part 61 electrically connects the first electrode 3 with conductor parts 516a, 516d as well as with a gate electrode of a transistor 514a. The conductor part 62 electrically connects the second electrode 4 with conductor parts 516b, 516e as well as with a gate electrode of a transistor 514b. Each of the first electrode 3 and the second electrode 4 is in a floating state because of the respective connections thereof with the gate electrodes of the transistors 514a, 514b. Reference numerals 515a and 515b indicate interlayer insulating films of the integrated circuit, and reference numeral 25 indicates a protective film of the integrated circuit.

The main body 2 also has a function for housing the functional element 51, the power source 52, the temperature sensor 53, the communication circuit 54, the antenna 55, and the oscillator 56.

In particular, the main body 2 is configured so as to provide a liquid-tight housing for the functional element 51, the power source 52, the temperature sensor 53, the communication circuit 54, the antenna 55, and the oscillator 56.

Specifically, as illustrated in FIGS. 4 and 5, the main body 2 has a sealing part 24. The sealing part 24 has a function for sealing in the functional element 51, the power source 52, the temperature sensor 53, the communication circuit 54, the antenna 55, and the oscillator 56. This makes it possible to prevent the deterioration of the functional element 51, the power source 52, the temperature sensor 53, the communication circuit 54, the antenna 55, and the oscillator 56 in a case where the sensor device 1 is installed in the presence of moisture or concrete.

Herein, the sealing part 24 has an opening part 241, and is provided such that each of the parts other than the first electrode 3 and the second electrode 4 are covered, while the first electrode 3 and the second electrode 4 are exposed from the opening part 241 (see FIGS. 3 and 4). This makes it possible for the sensor device 1 to measure while the sealing part 24 prevents each of the parts other than the first electrode 3 and the second electrode 4 from deteriorating. The opening part 241 may also be formed such that at least a part or more of the first electrode 3 and at least a part or more of the second electrode 4 is exposed.

Examples of materials which can be used to constitute the sealing part 24 include: a thermoplastic resin, such as an acrylic-based resin, a urethane-based resin, or an olefin-based resin; a thermosetting resin, such as an epoxy-based resin, a melamine-based resin, or a phenol-based resin; and various other types of resin materials, it being possible to use one type thereof or a combination of two or more types thereof.

The sealing part 24 may be provided or can be omitted, in accordance with need.

First Electrode and Second Electrode

The first electrode 3 and the second electrode 4, as illustrated in FIG. 4, are each provided on the outer surface of the main body 2 described above (more specifically, on the substrate 21). In particular, the first electrode 3 and the second electrode 4 are provided on the same plane. For this reason, it is possible to prevent the emergence of differences in the installation environments of the first electrode 3 and the second electrode 4.

The first electrode 3 and the second electrode 4 are spaced apart to such an extent (for example, several millimeters) that there is no mutual influence due to electric potential.

In the present embodiment, each of the first electrode 3 and the second electrode 4 forms the shape of a thin film. Each of the shapes in plan view of the first electrode 3 and the second electrode 4 also forms a quadrangle. The first electrode 3 and the second electrode 4 have mutually equivalent shapes and surface areas in plan view.

In particular, the first electrode 3, as illustrated in FIG. 6A, is constituted of a porous body 32 having a plurality of holes 31. The plurality of holes 31 form connecting holes (fine pores), where adjacent holes 31 communicate with each other, and the connecting holes provide openings on the surface of the first electrode 3.

Similarly, the second electrode 4, as illustrated in FIG. 6B, is constituted of a porous body 42 having a plurality of holes 41. The plurality of holes 41 form connecting holes (fine pores), where adjacent holes 41 communicate with each other, and the connecting holes provide openings on the surface of the second electrode 4.

Such connecting holes make it possible to give each of the first electrode 3 and the second electrode 4 a greater surface area. For this reason, the amount of moisture adhering to each of the first electrode 3 and the second electrode 4 can be increased.

The capillary condensation effect endowed by the fine pores makes it possible to cause moisture to condense on each of the first electrode 3 and the second electrode 4 at a lower relative humidity. For this reason, the presence of liquid water on each of the first electrode 3 and on the second electrode 4 can be rendered stable. Specifically, the presence of liquid water can be ensured through condensation on each of the first electrode 3 and the second electrode 4 even at a low relative humidity where condensation would not form on the first electrode 3 and on the second electrode 4 in a hypothetical case where the first electrode 3 and the second electrode 4 are constituted of compact bodies.

In view of such a fact, a fluctuation in the amount of moisture on the first electrode 3 and on the second electrode 4 can be prevented even though the relative humidity inside the concrete 101 may change in association with changes in the humidity or temperature of the external environment. Consequently, changes in the humidity or temperature of the external environment can be prevented from causing the self-potential of the first electrode 3 and the second electrode 4 to fluctuate, and the state of the site to be measured of the concrete 101 can be measured with a high degree of precision.

Preferably, the average diameter of the plurality of holes 31 and the plurality of holes 41 is, for example, 2 nm to 50 nm, but there is no particular limitation thereto, provided that the range thereof allows for the occurrence of the capillary condensation effect as described above. That is, preferably, the holes 31 and the holes 41 are mesopores. Also, the average diameter of the plurality of holes 31 and the average diameter of the plurality of holes 41 may be mutually identical or different.

Preferably, the porosity of each of the first electrode 3 and of the second electrode 4 is, for example, 10% to 90%, but there is no particular limitation thereto, provided that the range thereof allows for the occurrence of the capillary condensation effect as described above. The porosity of the first electrode 3 and the porosity of the second electrode 4 may be mutually identical or different.

In the present embodiment, the first electrode 3 and the second electrode 4 are constituted of mutually different materials. The following is a more detailed description of the constituent materials of the first electrode 3 and the second electrode 4.

Such a first electrode 3 is constituted of a first metallic material (which hereinafter is also simply called the "first metallic material") for forming a passivation film (a first passivation film). In the first electrode 3 having such a configuration, a passivation film is either formed or destroyed depending on changes in the pH. In the state where the passivation film has been so formed (the passivated state) on the first electrode 3, inactive (noble) conditions are in effect and self-potential increases (a shift towards increased nobility occurs). In the state where the passivation film has been destroyed (the state where the passivation film has been lost), the first electrode 3 is active (of less nobility). For this reason, the electric potential of the first electrode 3 has sharp changes depending on the presence or absence of the passivation film, as associated with changes in pH.

The first metallic material is not particularly limited, provided that a passivation film is formed; examples thereof include iron, nickel, magnesium, zinc, an alloy containing these elements, or the like.

For example, iron forms a passivation film when the pH is greater than 9 (see FIG. 9A). Iron-aluminum-based carbon steel (0.8% Al) also forms a passivation film when the pH is greater than 4 (see FIG. 9B). Nickel forms a passivation film when the pH is 8 to 14. Magnesium forms a passivation film when the pH is greater than 10.5. Zinc forms a passivation film when the pH is 6 to 12.

Of these, the first metallic material is preferably iron or an alloy containing iron (an iron-based alloy), i.e., an iron-based material (specifically, carbon steel, alloy steel, SUS, and the like). Iron-based materials are comparatively more readily and more inexpensively procured. In a case where, as in the present embodiment, the sensor device 1 is used to measure the state of the concrete structure 100, then the first metallic material can be a material identical to or approximating that of the reinforcing bars 102 of the concrete structure 100, and it is possible to effectively detect a state of a corrosive environment of the reinforcing bars 102. In the case where, for example, the first electrode 3 is constituted of iron, then a determination can be made as to whether or not the pH is 9 or greater.

On the other hand, the second electrode 4 is constituted of a second metallic material different from the first metallic material (which hereinafter is also simply called "the second metallic material"). A passivation film of the second electrode 4 having such a configuration is neither formed nor destroyed (lost), nor is there any sharp change in electric potential, when the electrode potential of the first electrode 3 changes depending on the presence or absence of the passivation film, as described above. For this reason, the difference in electric potential between the first electrode 3 and the second electrode 4 has sharp changes when the electric potential of the first electrode 3 changes depending on the presence or absence of the passivation film as described above. For this reason, it is possible to accurately detect whether or not the pHs of the installation environments of the first electrode 3 and the second electrode 4 (which, in this embodiment, are in the vicinity of the reinforcing bars 102 of the concrete 101) are at or below a set value.

Various types of metallic materials can be used as the second metallic material without particular limitation, provided that it is a metallic material in which the pH dependency with respect to the formation and/or loss of the passivation film is different from that of the first metallic material.

The second metallic material, with the provision of being a different metallic material from the aforesaid first metallic material, may form a passivation film or may not form a passivation film.

In a case where the second metallic material does form a passivation film (the second passivation film), then metals which can serve as the second metallic material include those examples provided for the first metallic material.

A preferred aspect of the present invention is that a first pH and a second pH are mutually different, where the first pH (a first passivation pH) is the lower limit of the range of pHs in which the first metallic material forms a passivation film, and the second pH (a second passivation pH) is the lower limit of the range of pHs in which the second metallic material forms a passivation film. That is, the first metallic material forms a passivation film when the pH thereof becomes greater than the first pH, and the second metallic material forms a passivation film when the pH thereof becomes greater than the second pH, which is different from the first pH. This makes it possible to accurately and respectively detect whether or not the pHs in the environments where the first electrode 3 has been installed and where the second electrode 4 has been installed are the first pH or lower or are the second pH or lower.

In such a case, preferably, the first pH is 8 to 10, and the second pH is 7 or lower. This also makes it possible, by detecting whether or not the pH is at or lower than the first pH, to know in advance that the installation environments of the first electrode 3 and the second electrode 4 are approaching a neutral state. In view of such facts, in a case where the sensor device 1 is used to measure the state of the concrete structure 100, as in this embodiment, it is possible to act in advance to counter and prevent the corrosion of the reinforcing bars 102. It is also possible, by detecting whether or not the pH is at or lower than the second pH, to know that the installation environments of the first electrode 3 and the second electrode 4 have reached an acidic state.

In such a case, preferably, the second metallic material is iron or an alloying containing iron (an iron-based alloy), i.e., an iron-based material. Iron-based materials are comparatively more readily and more inexpensively procured. Further, in a case where the sensor device 1 is used to measure the state of the concrete structure 100, as in this embodiment, then it is possible for the second metallic material to be the same material as the reinforcing bars 102. Having the second metallic material be the same material as the reinforcing bars 102 makes it possible to effectively detect the state of corrosion of the reinforcing bars 102.

On the other hand, in a case where the second metallic material does not form a passivation film, then possible examples of the second metallic material include platinum, gold, and the like. In a case where the second metallic material does not form a passivation film, then it is possible to know in a single stage, with a high degree of precision, the change when the installation environments of the first electrode 3 and the second electrode 4 change from a strongly alkaline state to a strongly acidic state.

In such a case, preferably, the first metallic material forms a passivation film when the pH thereof becomes greater than a pH of 3 to 5, or, greater than a pH of 8 to 10. It is possible, by detecting whether or not the pH is a pH of at or lower than a pH of 3 to 5, to know that the installation environments of the first electrode 3 and the second electrode 4 have reached an acidic state. Detecting whether or not the pH is at or below a pH of 8 to 10 also makes it possible to know in advance that the installation environments of the first electrode 3 and the second electrode 4 are approaching a neutral state.

According to another aspect of the present invention, a case where the second metallic material does form a passivation film involves a first chloride ion concentration and a second chloride ion concentration, which are mutually different, where the first chloride ion concentration is the lower limit of the chloride ion concentration at which the passivation film of the first metallic material begins to be destroyed and the second chloride ion concentration is the lower limit of the chloride ion concentration at which the passivation film of the second metallic material begins to be destroyed. That is, the passivation film of the first metallic material begins to be destroyed when the chloride ion concentration becomes greater than the first chloride ion concentration, and the second metallic material begins to disintegrate when the chloride ion concentration becomes greater than the second chloride ion concentration. This makes it possible to accurately and respectively detect whether or not the chloride ion concentrations of the environments where the first electrode 3 has been installed and where the second electrode 4 has been installed are at or below the first chloride ion concentration or are at or below the second chloride ion concentration.

In view of such facts, in the case where the sensor device 1 is used to measure the state of the concrete structure 100, as in this embodiment, then it is possible to detect $CO_2$ (neutralization) and chloride ions infiltrating into the concrete from outside, before the reinforcing bars 102 inside the concrete structure 100 are reached. Accordingly, it is possible to act to counter and prevent corrosion before the reinforcing bars 102 are corroded.

Each of such a first electrode 3 and a second electrode 4 is not particularly limited and can be formed by a known method for forming a porous body film. The shapes of the plurality of holes 31 and the plurality of holes 41 illustrated in FIG. 6 are each one example, there being no limitation to what has been depicted, provided that the first electrode 3 and the second electrode 4 be able to exert the capillary condensation effect as described above. The first electrode 3 and the second electrode 4 can be constituted of various known porous bodies having connecting holes.

Functional Element

The functional element 51 is embedded in the interior of the aforesaid main body 2. The surface of the substrate 21 of the main body 2 to which the functional element 51 is provided may be identical to or opposite from that of the first electrode 3 and the second electrode 4.

The functional element 51 has a function for measuring the difference in electric potential between the first electrode 3 and the second electrode 4. This makes it possible to detect whether or not the pHs of the installation environments of the first electrode 3 and the second electrode 4 are at or below a set value, based on the difference in electric potential between the first electrode 3 and the second electrode 4.

The functional element 51 also has a function for detecting whether or not the pH or chloride ion concentration of the site to be measured of the concrete structure 100, which is the object to be measured, is at or below a set value, based on the difference in electric potential between the first electrode 3 and the second electrode 4. This makes it possible to detect a change in state of the concrete structure 100 in association with a change in the pH or a change in the chloride ion concentration thereof.

Such a functional element 51 is, for example, an integrated circuit. More specifically, the functional element 51 is, for example, an MCU (a micro control unit) and has, as illustrated in FIG. 2, a CPU 511, an A/D conversion circuit 512, and a differential amplifier circuit 514.

A more specific description shall now be provided. The functional element 51, as illustrated in FIG. 5, has: a substrate 513; a plurality of transistors 514a, 514b, 514c provided on the substrate 513; interlayer insulating films 515a, 515b for covering the transistors 514a, 514b, 514c; conductor parts 516a, 516b, 516c, 516d, 516e, 516f constituting a wiring and a conductor post; a protective film 25; and conductor parts 61, 62 constituting an electrode pad.

The substrate 513 is, for example, an SOI substrate, on which the CPU 511 and the A/D conversion circuit 512 are formed. Using an SOI substrate as the substrate 513 makes it possible to make the transistors 514a to 514c into an SOI-type MOSFET.

The plurality of transistors 514a, 514b, 514c are each, for example, field-effect transistors (FETs), and constitute a part of the differential amplifier circuit 514.

The differential amplifier circuit 514, as illustrated in FIG. 7, is constituted of the three transistors 514a to 514c as well as a current mirror circuit 514d.

The differential amplifier circuit 514 also has operating amplifiers 201, 202 and an operating amplifier 203, as illustrated in FIG. 8.

The operating amplifier 201 detects the electric potential of the first electrode 3 using a comparative electrode 7 as a reference. The operating amplifier 202 detects the electric potential of the second electrode 4 using the comparative electrode 7 as a reference. The operating amplifier 203 detects the difference between the outputted electric potential of the operating amplifier 201 and the outputted electric potential of the operating amplifier 202.

The conductor part 516a has one end connected to a gate electrode of the transistor 514a, and another end connected to the aforesaid conductor part 516d. The conductor part 516d is electrically connected to the first electrode 3 via the conductor part 61. An electrical connection is thereby formed between the first electrode 3 and the gate electrode of the transistor 514a. For this reason, the drain current of the transistor 514a changes in accordance with changes in the electric potential of the first electrode 3.

Similarly, the conductor part 516b has one end connected to a gate electrode of the transistor 514b, and another end connected to the aforesaid conductor part 516e. The conductor part 516e is electrically connected to the second electrode 4 via the conductor part 62. An electrical connection is thereby formed between the second electrode 4 and the gate electrode of the transistor 514b. For this reason, the drain current of the transistor 514b changes in accordance with changes in the electric potential of the second electrode 4.

The conductor part 516c has one end connected to a gate electrode of the transistor 514c, and another end connected to the aforesaid conductor part 516f, thus constituting a part of a circuit.

The functional element 51 is operated by energization from the power source 52. Provided that the power source 52 can supply electric power capable of operating the functional element 51, there is no particular limitation, and the power source 52 may be, for example, a battery such as a button-type battery, or may be a power source using an element having a power generation function, such as a piezoelectric element.

The functional element 51 is configured so as to be able to acquire detected temperature information on the temperature sensor 53. This makes it possible also to obtain information relating to the temperature of the site to be measured. The use of such information relating to the temperature makes it possible to more accurately measure the state of the site to be measured, or to anticipate changes in the site to be measured with a high degree of precision.

The temperature sensor 53 has a function for detecting the temperature of the site to be measured of the concrete structure 100, which is the object to be measured. Examples of temperature sensors which can be used as such a temperature sensor 53 include but are not particularly limited to a thermocouple or other various known types.

The functional element 51 also has a function for driving and controlling the communication circuit 54. For example, the functional element 51 respectively inputs, into the communication circuit 54, information relating to the difference in electric potential between the first electrode 3 and the second electrode 4 (which hereinafter is also simply called "electric potential difference information") as well as information relating to whether or not the pH or chloride ion concentration of the site to be measured is at or below a set value (which hereinafter is also simply called "pH information"). The functional element 51 also additionally inputs, into the communication circuit 54, information relating to the temperature detected by the temperature sensor 53 (which hereinafter is also simply called "temperature information").

The communication circuit 54 has a function for supplying power to the antenna 55 (a transmitting function). This makes it possible for the communication circuit 54 to wirelessly transmit inputted information via the antenna 55. The transmitted information is received by a receiver (reader) provided outside the concrete structure 100.

The communication circuit 54 has, for example, a transmission circuit for transmitting electromagnetic waves, a modulation circuit having a function for modulating a signal, and the like. The communication circuit 54 may also have a down converter circuit having a function for converting a signal to a lower frequency, an up converter having a function for converting a signal to a higher frequency, an amplifier circuit having a function for amplifying a signal, a receiving circuit for receiving electromagnetic waves, a demodulating circuit having a function for demodulating a signal, and the like.

The antenna 55 is constituted of for example, a metallic material, carbon, or the like, but is not particularly limited thereto, and forms a winding wire, a thin film, or another form.

The functional element 51 is configured so as to be able to acquire a clock signal from the oscillator 56. This makes it possible to synchronize each of the circuits, or to add time information to each of the various forms of information.

The oscillator 56 is constituted of, for example, an oscillation circuit employing a crystal oscillator, but is not particularly limited thereto.

In a measurement method using the sensor device 1 configured as has been described above, the first electrode 3 and the second electrode 4 are each embedded in the concrete structure 100, which is the object to be measured, and the state of the concrete structure 100 is measured based on the difference in electric potential between the first electrode 3 and the second electrode 4.

The following is a description of the action of the sensor device 1 using, by way of example, a case where the first electrode 3 is constituted of iron and the second electrode 4 is constituted of iron-aluminum.

Figure 10A:
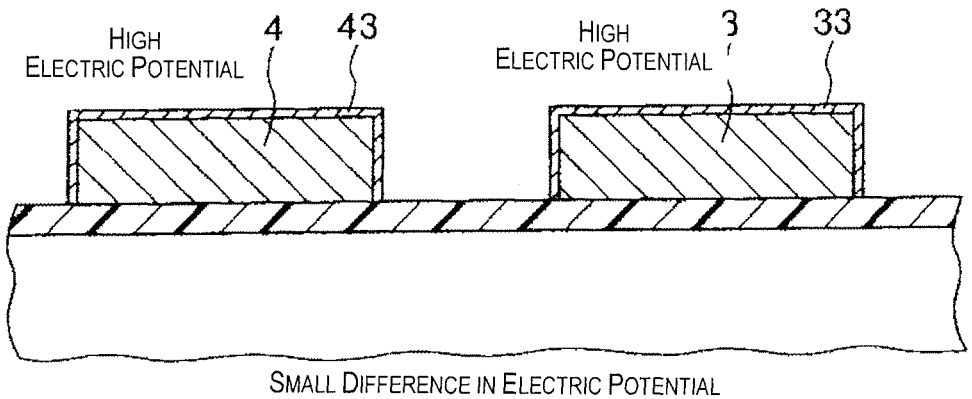
FIG. 10 is a drawing for describing an example of the action of the sensor device illustrated in FIG. 1.

In the concrete structure 100 immediately after casting, ordinarily, the concrete 101 exhibits a strong alkalinity when casting has been done appropriately. For this reason, at such a time, the first electrode 3 and the second electrode 4 each forms stable passivation films, as illustrated in FIGS. 9A and 9B. That is, as illustrated in FIG. 10A, a passivation film 33 is formed on the surface of the first electrode 3, and a passivation film 43 is formed on the surface of the second electrode 4. The self-potentials of the first electrode 3 and the second electrode 4 are thereby each made to increase (become more noble). As a result, the difference in electric potential between the first electrode 3 and the second electrode 4 immediately after the concrete has been cast is reduced.

Thereafter, the pH of the concrete 101 in the concrete structure 100 gradually changes toward becoming acidic due to the effects of carbon dioxide, acidic rain, exhaust gas, and the like.

Figure 10B:
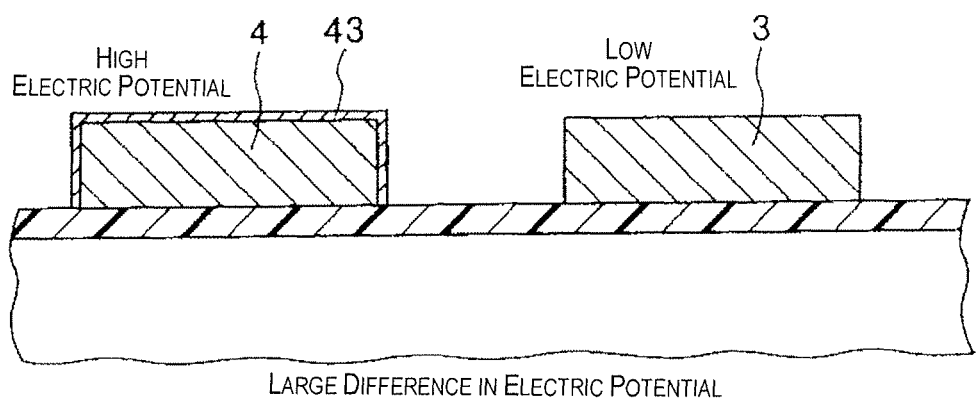

When the pH of the concrete 101 drops to as low as about 9, then, as illustrated in FIG. 10B, although the passivation film 43 of the second electrode 4 is stable and the self-potential thereof changes only slightly, the passivation film of the first electrode 3 begins to disintegrate, and thus the self-potential thereof drops (becomes less noble). The difference in electric potential between the first electrode 3 and the second electrode 4 is thereby increased.

Figure 10C:
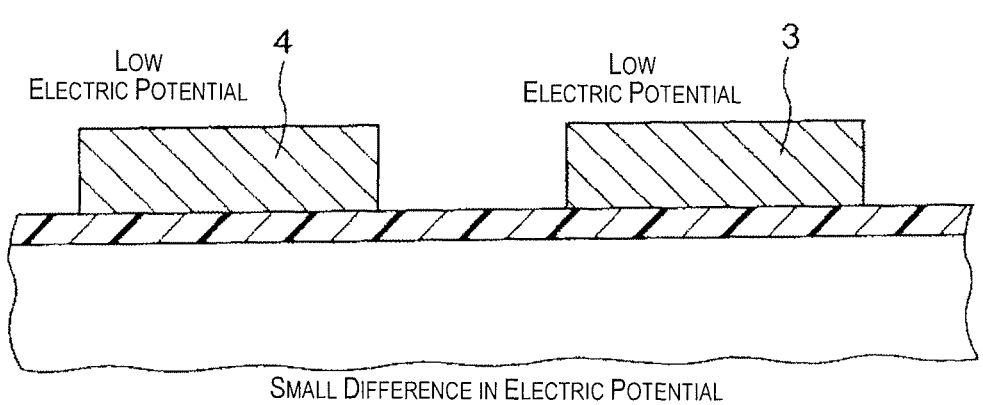

When the pH of the concrete 101 drops to as low as about 4, then, as illustrated in FIG. 10C, the passivation film of the second electrode 4 also begins to disintegrate, and the self-potential thereof drops. At such a time, because the self-potentials of both the first electrode 3 and the second electrode 4 drop, the difference in electric potential between the first electrode 3 and the second electrode 4 is once again reduced. At such a time, each of the first electrode 3 and the second electrode 4 is undergoing progressive corrosion.

Thus, the difference in electric potential between the first electrode 3 and the second electrode 4 has sharp changes at two different times, which are the time when the pH reaches about 9 and the time when the pH reaches about 4. For this reason, it is possible to respectively detect with a high degree of precision that the pH of the site to be measured has reached about 9, and that the pH of the site to be measured has reached about 4.

The use of such detection results makes it possible to monitor for a long time the temporal changes in the qualities of the concrete structure 100 after casting. For this reason, it is possible to become aware of the deterioration of the concrete 101 (neutralization or the intrusion of saline matter) before the reinforcing bars 102 are corroded. This makes it possible to paint the concrete structure 100 or perform repair work by a mixed anti-corrosion agent mortar or the like, before the reinforcing bars 102 are corroded.

It is also possible to determine whether or not there has been any abnormality during the casting of the concrete structure 100. For this reason, it is possible to prevent initial difficulties with the concrete structure 100, and to improve the quality of the concrete structure 100.

According to the sensor device 1 of the first embodiment as has been described above, because each of the first electrode 3 and the second electrode 4 is constituted of a porous body having connecting holes, each of the first electrode 3 and the second electrode 4 can be given a greater surface area. For this reason, the amount of moisture adhering to each of the first electrode 3 and the second electrode 4 can be increased.

The capillary condensation effect endowed by the connecting holes (fine pores) of the first electrode 3 and of the second electrode 4 makes it possible to cause moisture to condense on each of the first electrode 3 and the second electrode 4 at a lower relative humidity. For this reason, a stable presence of liquid water can be maintained on the first electrode 3 and on the second electrode 4.

In view of such a fact, a fluctuation in the amount of moisture on the first electrode 3 and on the second electrode 4 can be prevented even though the relative humidity inside the concrete 101 may change in association with changes in the humidity or temperature of the external environment. Consequently, changes in the humidity or temperature of the external environment can be prevented from causing the self-potential of the first electrode 3 and the second electrode 4 to fluctuate, and the state of the site to be measured of the concrete 101 can be measured with a high degree of precision.

Second Embodiment

The following is a description of a second embodiment of the present invention.

Figure 11:
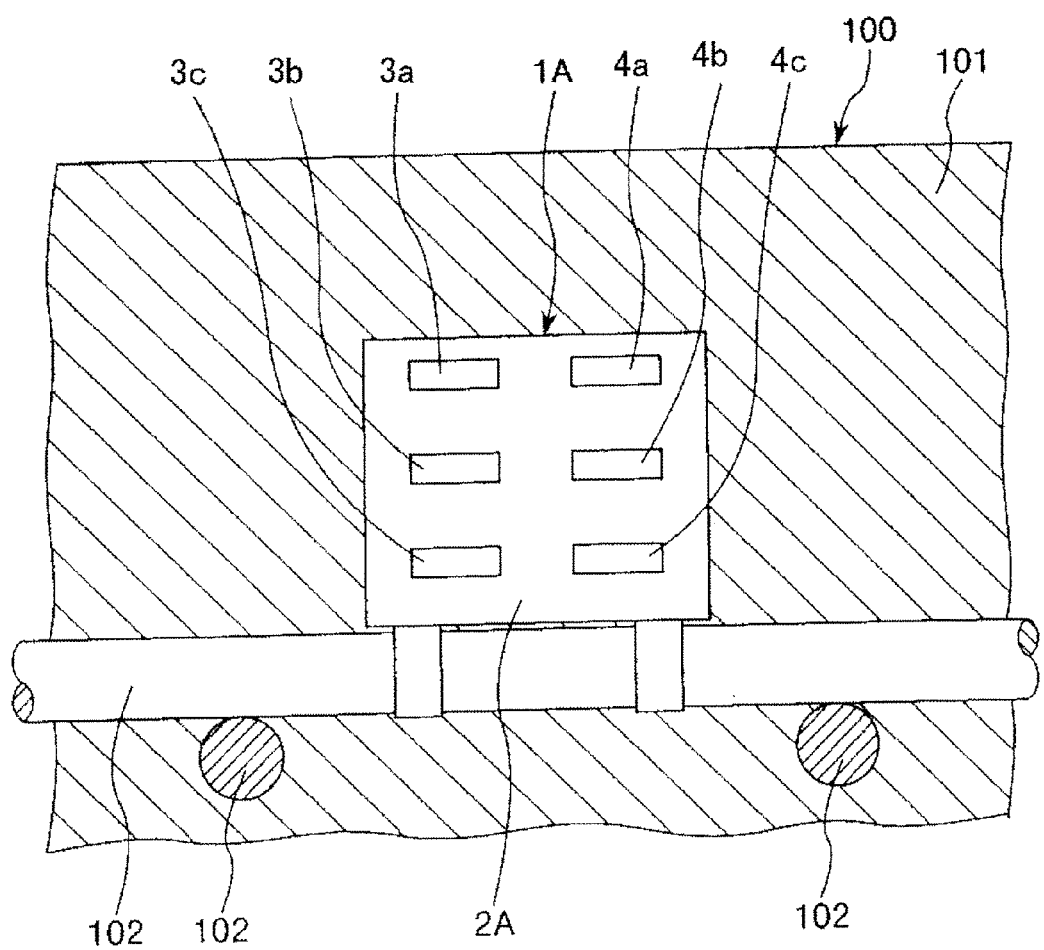
FIG. 11 is a drawing illustrating an example of the state of use of a sensor device according to a second embodiment of the present invention.
Figure 12A:
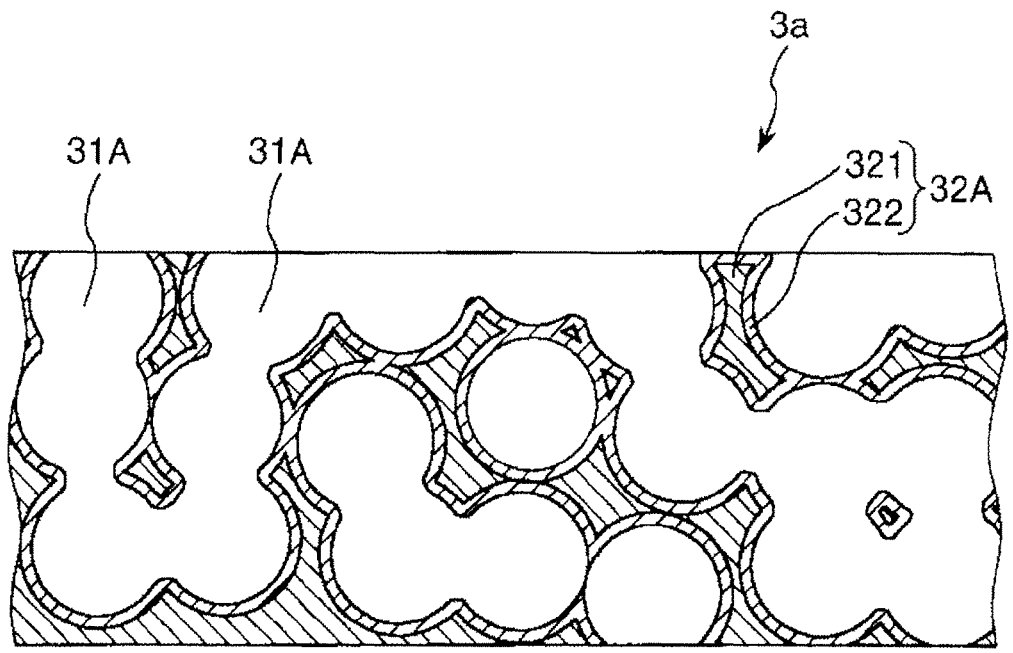
FIG. 12A is an enlarged sectional view illustrating an example of a configuration of the first electrode illustrated in FIG. 11.

FIG. 11 is a drawing illustrating an example of the state of use of a sensor device according to a second embodiment of the present invention. FIG. 12A is an enlarged sectional view illustrating an example of a configuration of the first electrode illustrated in FIG. 11.

Figure 12B:
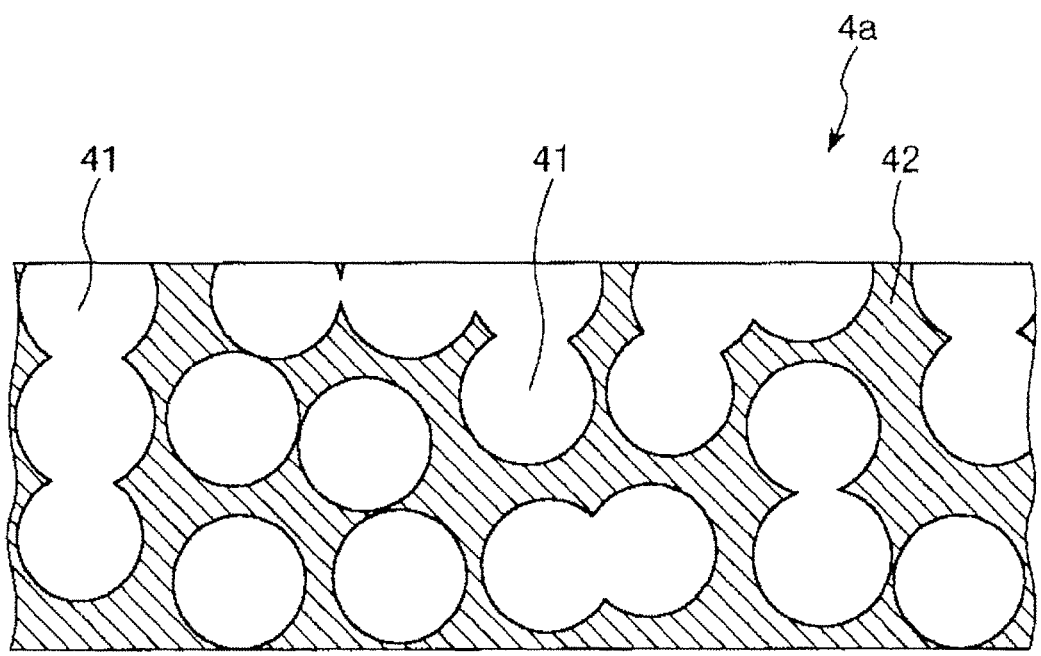
FIG. 12B is an enlarged sectional view illustrating an example of a configuration of the second electrode illustrated in FIG. 11.

FIG. 12B is an enlarged sectional view illustrating an example of a configuration of the second electrode illustrated in FIG. 11.

The following description of the second embodiment focuses on the points of difference with the embodiment described above, and omits a description of any similar matters.

The sensor device of the second embodiment is substantially similar to the sensor device of the first embodiment, except in that the shapes in plan view and number of the first electrode and the second electrode are different, and in that the structure of the first electrode is different. Constituent elements which are similar to the embodiment described above have been assigned like reference numerals.

A sensor device sensor device 1A of this embodiment has a main body 2A, as well as a plurality of first electrodes 3a, 3b, 3c and a plurality of second electrodes 4a, 4b, 4c exposed to the surface of the main body 2A.

In this embodiment, the first electrodes 3a, 3b, 3c and the second electrodes 4a, 4b, 4c are provided mutually spaced apart. Also, the first electrodes 3a, 3b, 3c and the second electrodes 4a, 4b, 4c are each installed such that the electrode surface becomes perpendicular to or substantially perpendicular to the outer surface of the concrete structure 100.

The plurality of first electrodes 3a, 3b, 3c are all at mutually different distances from the outer surface of the concrete structure 100. Specifically, the plurality of first electrodes 3a, 3b, 3c are provided lined up in the stated order, from the outer surface of the concrete structure 100 inward.

Similarly, the plurality of second electrodes 4a, 4b, 4c are all at mutually different distances from the outer surface of the concrete structure 100. Specifically, the plurality of second electrodes 4a, 4b, 4c are provided lined up in the stated order, from the outer surface of the concrete structure 100 inward.

Furthermore, the first electrode 3a and the second electrode 4a are installed so as to both be equidistant from the outer surface of the concrete structure 100. The first electrode 3b and the second electrode 4b are installed so as to both be equidistant from the outer surface of the concrete structure 100. The first electrode 3c and the second electrode 4c are installed so as to both be equidistant from the outer surface of the concrete structure 100.

With such first electrodes 3a, 3b, 3c and second electrodes 4a, 4b, 4c, the first electrodes 3a, the first electrode 3a and the second electrode 4a form a pair, the first electrode 3b and the second electrode 4b form a pair, and the first electrode 3c and the second electrode 4c form a pair.

In the present embodiment, the sensor device 1A is configured such that the difference in electric potential between the first electrode 3a and the second electrode 4a, the difference in electric potential between the first electrode 3b and the second electrode 4b, and the difference in electric potential between the first electrode 3c and the second electrode 4c can each be measured by a functional element (not shown).

Herein, a more detailed description of the first electrode 3a and the second electrode 4a shall now be provided. Each of the configurations of the first electrode 3b and the first electrode 3c is similar to the configuration of the first electrode 3a, and each of the configurations of the second electrode 4b and the second electrode 4c is similar to the configuration of the second electrode 4a.

In the present embodiment, as illustrated in FIG. 12A, the first electrode 3a is constituted of a porous body 32A having connecting holes, where adjacent holes 31A communicate with each other. The porous body 32A is provided with a substrate 321, as well as with a conductive film 322 provided on the substrate 321 and constituted of a different material from that of the substrate 321.

Having the first electrode 3a so constituted from the substrate 321 and the conductive film 322 makes it possible to have the conductive film 322 (the vicinity of the surface of the first electrode 3a) constituted of a metal from which it is difficult to produce a porous body. The thickness of the conductive film 322 can also be used to adjust the hole diameter of the porous body constituting the first electrode 3a.

The constituent material of the substrate 321 of the first electrode 3a of such description may be a material having conductivity, and, in addition to the constituent materials of the first electrode 3 in the first embodiment described above (the first metallic material), a conductive ceramic can also be used.

The constituent material of the first electrode 3 in the first embodiment described above (the first metallic material) can also be used as the constituent material of the conductive film 322.

Such a first electrode 3a is obtained, for example, by the formation of the substrate 321, which is a porous body, and the formation of the conductive film 322 on the substrate 321 using electroplating or another technique.

In particular, preferably, the conductive film 322 is constituted of a metallic material in which either a passivation film is formed on a surface thereof or a passivation film present on a surface thereof is lost, in association with changes in the environment of the site to be measured.

Thereby, the difference in electric potential between the first electrode 3a and the second electrode 4a has sharp changes depending on the presence or absence of the passivation film, which is associated with changes in pH of the site to be measured. For this reason, it is possible to accurately measure whether or not the pH of the site to be measured is at or below a set value.

The difference in electric potential between the first electrode 3a and the second electrode 4a also has sharp changes depending on the loss of the passivation film, which is associated with changes in the chloride ion concentration of the site to be measured. For this reason, it is possible to accurately measure whether or not the chloride ion concentration of the site to be measured is at or below a set value.

By contrast, as illustrated in FIG. 12B, the second electrode 4a is, similarly with respect to the second electrode 4 in the first embodiment described above, constituted of a porous body 42 having connecting holes, where adjacent holes 41 communicate with each other.

The second electrode 4a, too, similarly with respect to the first electrode 3a, may be constituted of a porous body provided with a substrate as well as with a conductive film provided on the substrate.

According to such a sensor device 1A according to the second embodiment, it is possible to accurately detect whether or not the pHs of the installation environments of the first electrode 3a and the second electrode 4a, the installation environments of the first electrode 3b and the second electrode 4b, and the installation environments of the first electrode 3c and the second electrode 4c are at or below a set value. It is possible to measure the respective differences in electric potential and, therefore, to accurately detect whether or not the pH of the installation environments of the first electrodes 3a, 3b, 3c and of the second electrodes 4a, 4b, 4c is at or below a set value. That is, it is possible to accurately detect whether or not the pH at positions of different depths from the outer surface of the concrete structure 100 is at or below a set value. This makes it possible to detect the speed at which the pH of the concrete 101 is changing toward being more acidic. For this reason, it is possible to effectively predict the infiltration of neutralization (or salt damage) in the depth direction of the concrete structure 100.

The preceding is a description of the sensor device of the present invention, based on the depicted embodiments, but the present invention is in no way limited thereto.

For example, the configuration of each of the parts in the sensor device of the present invention can be substituted with any desired configuration for exerting similar functions, and any desired configuration can be added.

Also, the embodiments described above are descriptions, by way of example, of a case where each of the first electrode and the second electrode is provided on the substrate, but there is no limitation thereto, and, for example, the first electrode and the second electrode may also be provided, for example, on the outer surface of the portion of the main body of the sensor device constituted of the sealing resin.

Further, the embodiments described above are descriptions, by way of example, of a case where the first electrode and the second electrode each form the shape of a thin film, but there is no limitation thereto, and the shapes of the first electrode and the second electrode may also each form, for example, a block shape, a wire shape, or the like. In the embodiments described above, the first electrode and the second electrode are each provided along the outer surface of the main body of the sensor device, but the first electrode and the second electrode may also each be projected out from the outer surface of the main body of the sensor device. In addition, the installation locations, size (relative sizes), and other aspects of the first electrode and the second electrode are also not limited by the embodiments described above, and may be as desired provided that measurement as described above is possible.

Also, the embodiments described above are descriptions, by way of example, of a case where the functional element has a CPU, an A/D conversion circuit, and a differential amplifier circuit, but there is no limitation thereto, and, for example, a ROM, RAM, various types of drive circuits, and other, additional circuits may be incorporated into the functional element.

The embodiments described above are descriptions, by way of example, of a case where information relating to the difference in electric potential between the first electrode and the second electrode is transmitted outside the sensor device by active tag communication by wireless transmission, but there is no limitation thereto, and, for example, passive tag communication may be used to transmit the information outside the sensor device, or the information may be transmitted outside the sensor device by wire.

The embodiments described above are descriptions, by way of example, of a case where the functional element 51, the power source 52, the temperature sensor 53, the communication circuit 54, the antenna 55, and the oscillator 56 are housed in the main body 2, and these elements is are, together with the first electrode 3 and the second electrode 4, embedded in the concrete structure 100, which is the object to be measured, but the functional element 51, the power source 52, the temperature sensor 53, the communication circuit 54, the antenna 55, and the oscillator 56 may also be provided outside the object to be measured.

The embodiments described above are descriptions, by way of example, of a case where both the first electrode and the second electrode are constituted of porous bodies, but the effects of the present invention can be achieved whenever at least one electrode or more of the first electrode and the second electrode is constituted of a porous body.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A sensor device comprising:
    a first electrode being constituted of a porous body that has a plurality of holes in at least the vicinity of a surface of the first electrode, an average diameter of the plurality of the holes being in a range that allows for occurrence of a capillary condensation effect, the first electrode being integrated as a one piece, unitary metallic member, the first electrode including a first metallic material in which either a first passivation film is formed on a surface thereof or a first passivation film present on a surface thereof is lost, in association with changes in an environment of the site to be measured, the first metallic material having a first pH dependency with respect to at least one of formation and loss of the first passivation film;
    a second electrode spaced apart from the first electrode, the second electrode including a second metallic material in which either a second passivation film is formed on a surface thereof or a second passivation film present on a surface thereof is lost, in association with changes in the environment of the site to be measured, the second metallic material having a second pH dependency with respect to at least one of formation and loss of the second passivation film, the second pH dependency being different from the first pH dependency; and
    a functional element configured to measure a difference in electric potential between the first electrode and the second electrode,
    the sensor device being configured to measure a state of a site to be measured based on the difference in electric potential as measured by the functional element.

2. The sensor device according to claim 1, wherein
    the second electrode is constituted of a porous body that has a plurality of holes in at least the vicinity of a surface of the second electrode, and an average diameter of the plurality of the holes is in a range that allows for occurrence of a capillary condensation effect.

3. The sensor device according to claim 2, wherein
    at least one of the first electrode and the second electrode includes a substrate and a conductive film provided on the substrate including a material different from that of the substrate.

4. The sensor device according to claim 3, wherein
    the conductive film includes a metallic material in which either a passivation film is formed on a surface thereof or a passivation film present on a surface thereof is lost, in association with changes in an environment of the site to be measured.

5. The sensor device according to claim 1, wherein
    each of the first metallic material and the second metallic material is iron or an iron-based alloy.

6. The sensor device according to claim 1, wherein
    the functional element is further configured to detect whether or not pH or chloride ion concentration at the site to be measured is at or below a set value, based on the difference in electric potential between the first electrode and the second electrode.

7. The sensor device according to claim 1, further comprising
    an antenna and a communication circuit configured to provide power to the antenna,
    the functional element being further configured to drive and control the communication circuit.

8. The sensor device according to claim 1, wherein
    the first metallic material of the first electrode has a first range of pHs where the first passivation film is formed, the second metallic material of the second electrode has a second range of pHs where the second passivation film is formed, the first range of pHs has a first passivation pH that is a lower limit of the first range of pHs, and the second range of pHs has a second passivation pH that is a lower limit of the second range of pHs and different from the first passivation pH.

\* \* \* \* \*